United States Patent
Zacouto

(10) Patent No.: US 9,249,412 B2
(45) Date of Patent: Feb. 2, 2016

(54) SIMPLIFIED METHOD FOR PARTIAL GENETIC AND EPIGENETIC REPROGRAMMING OF CELLS USING SIRNA SPECIFIC FOR A HETEROCHROMATIN PROTEIN 1

(76) Inventor: Fred Zacouto, Paris (FR)

( * ) Notice: Subject to any disclaimer, the term of this patent is extended or adjusted under 35 U.S.C. 154(b) by 612 days.

(21) Appl. No.: 13/146,158

(22) PCT Filed: Jan. 7, 2010

(86) PCT No.: PCT/FR2010/050022
§ 371 (c)(1),
(2), (4) Date: Jul. 25, 2011

(87) PCT Pub. No.: WO2010/084275
PCT Pub. Date: Jul. 29, 2010

(65) Prior Publication Data
US 2011/0287536 A1    Nov. 24, 2011

(30) Foreign Application Priority Data

Jan. 26, 2009  (FR) ...................................... 09 50466
Oct. 9, 2009   (FR) ...................................... 09 57075

(51) Int. Cl.
C12N 5/075   (2010.01)
C12N 15/113  (2010.01)
C12N 5/16    (2006.01)
C12N 15/63   (2006.01)
C12N 5/074   (2010.01)
C12N 15/11   (2006.01)

(52) U.S. Cl.
CPC ............. *C12N 15/113* (2013.01); *C12N 5/16* (2013.01); *C12N 5/0696* (2013.01); *C12N 15/111* (2013.01); *C12N 15/63* (2013.01); *C12N 2310/14* (2013.01); *C12N 2310/141* (2013.01); *C12N 2500/84* (2013.01); *C12N 2501/60* (2013.01); *C12N 2502/1335* (2013.01); *C12N 2506/00* (2013.01); *C12N 2506/11* (2013.01); *C12N 2506/1307* (2013.01); *C12N 2506/45* (2013.01); *C12N 2510/00* (2013.01); *C12N 2517/04* (2013.01)

(58) Field of Classification Search
CPC ............. C12N 5/0696; C12N 15/113; C12N 2501/60; C12N 2310/141; C12N 2500/84; C12N 2310/14; C12N 2502/1335; C12N 2506/11; C12N 2506/1307; C12N 2506/45; C12N 15/111; C12N 2506/00; C12N 5/16; C12N 2510/00; C12N 15/63
See application file for complete search history.

(56) References Cited

U.S. PATENT DOCUMENTS

2006/0252062 A1 *  11/2006  Zaccouto ..................... 435/6

FOREIGN PATENT DOCUMENTS

WO    01/00650 A1    1/2001
WO    02/057415 A2   7/2002
WO    2007/000523 A2 1/2007

OTHER PUBLICATIONS

Takanashi et al. Heterochromatin Protein 1 Epigenetically Regulates Cell Differentiation and Exhibits Potential as a Therapeutic Target for Various Types of CancersAmerican J. Pathology, 2009, Epub Dec. 4, 2008, vol. 174, pp. 309-316, DOI:10.2353/ajpath.2009.080148.*
Gazzar et al. G9a and HP1 Couple Histone and DNA Methylation to TNFa Transcription Silencing during Endotoxin Tolerance. Journal of Biological Chemistry, 2008, vol. 283, pp. 32198-32208.*
Zhang et al. Formation of MacroH2A-Containing Senescence-Associated Heterochromatin Foci and Senescence Driven by ASF1a and HIRA. Developmetnal Cell, 2005, vol. 8, pp. 19-30.*
Irina Panteleeva et al., "HP1 alpha guides neuronal fate by timing E2F-targeted genes during terminal differentiation," The EMBO Journal, vol. 26, 2007, pp. 3616-3628.
Prim B. Singh et al., "Nuclear reprogramming and epigenetic rejuvination," Journal of Biosciences, vol. 35, No. 2, Apr. 2010, pp. 1-5.

* cited by examiner

*Primary Examiner* — Deborah Crouch
(74) *Attorney, Agent, or Firm* — Sughrue Mion, PLLC

(57) ABSTRACT

A method of partial, rapid and direct genetic and epigenetic reprogramming of biological cells without returning to the embryonic state can partially reprogram a cell to be treated to specifically modify the biological age of said cell to be treated without causing functional de-differentiation of said cell to be treated, said cell to be treated always remaining as a specialized functional cell that is immunologically autologous to the donor tissue from which said cell to be treated is derived, and for which the phenotype is preserved and/or rejuvenated.

10 Claims, No Drawings

SIMPLIFIED METHOD FOR PARTIAL GENETIC AND EPIGENETIC REPROGRAMMING OF CELLS USING SIRNA SPECIFIC FOR A HETEROCHROMATIN PROTEIN 1

CROSS REFERENCE TO RELATED APPLICATIONS

This application is a National Stage of International Application No. PCT/FR2010/050022, filed on Jan. 7, 2010, which claims priority from French Patent Application Nos. 09 50466 filed on Jan. 26, 2009 and 09 57075 filed on Oct. 9, 2009, the contents of all of which are incorporated herein by reference in their entirety.

The present invention relates to partial genetic and epigenetic reprogramming, in particular rejuvenation, of biological cells such as specialized adult cells, in particular to regenerate and/or increase their specific functions, their immunogenicity and their lifespan.

In particular, said rejuvenation is of use in the field of cell treatments, in particular for carrying out autografts from differentiated cells that have become insufficient due to their biological age or their state of functional health, as well as for obtaining extracts capable of genetically reinvigorating a type of tissue. Cell treatments, in particular autografts, especially those that are genetically manipulated, are currently carried out with the aim of repairing tissue damaged by a disease, a cellular deficit, or necrosis. That technique frequently consists in removing a few healthy cells from the tissue concerned, in placing them under multiplication cell culture in order to form a cellular stock or tissue, and then in re-implanting those cells into the tissue to be treated, or else in initially de-differentiating those cells to the embryonic state using a few factors imported into their cytoplasm and/or nucleus, and then in artificially re-differentiating them. The results obtained, however, still cannot be used in man.

Thus, reprogramming of cells to create embryonic stem cells is known. During that cellular de-differentiation, DNA and its chromatins and heterochromatins are changed, in particular as regards the methyl radicals that activate inhibited genes. The cells obtained thereby are termed induced pluripotent stem cells (iPS). During subsequent artificial differentiation of those stem cells, a portion of the epigenetic information is lost; in particular, the phenotype of the original cell is not maintained in all of its specificity and stability, and so the cell loses some memory of its origin. The article by Valery Krizhanovsky & Scott W. Lowe ("Stem Cells: The promises and perils of p53"; NATURE, advance online publication; 12 Aug. 2009; doi: 10.1038/nature8367; published online on 12 Aug. 2009) indicates a reduction in the p53 gene, which gives rise to risks of cellular instability and cancers. Thus, for now, those techniques are unsuitable for man. The invention proposes direct, rapid partial cellular reprogramming, in contrast to current stem cell methods that use lengthy, indirect routes since they initially require adult cells to return artificially to the embryonic state and then artificial differentiation is carried out, risking a certain amount of genetic instability.

The documents WO 2005/046790 and US 2006/0252062 describe a method known as "partial cloning", which consists of temporarily transferring a nucleus from a cell to be treated into a genetic reprogramming medium, in particular an enucleated oocyte. The manipulation and transfer of nuclei isolated from cells is relatively complex and thus fairly difficult.

The aim of the present invention is to provide systems and methods of epigenetic reprogramming that do not suffer from the disadvantages mentioned above.

In particular, the present invention is aimed at rejuvenating a cell, thereby preserving specific transcription factors of the cell line in order to maintain all of its autologous immunological specificity relative to the original tissue.

In particular, the present invention aims to provide systems and methods of genetic and epigenetic reprogramming of cells that can reduce the biological age of treated cells, such as suppressing cell senescence, without ever inducing total functional de-differentiation thereof.

More particularly, the present invention aims to carry out partial cellular reprogramming that in particular maintains the functional and immunological specificities of the cell (monopotent reprogramming) as it is carried out.

The present invention also aims to restart a plurality of viable successive mitoses in definitively quiescent senescent cells or in abnormal mitosis, to generate genetically rejuvenated mitosis, and also to genetically rejuvenate cells independently of their mitosis.

The present invention is also intended to provide a partial cellular reprogramming method that is simple, cheap, and rapid to carry out and use.

Thus, the present invention provides a method of genetic and epigenetic reprogramming of biological cells, comprising partially reprogramming a cell to be treated, without returning it to its embryonic state, to modify the biological age of said cell to be treated without causing functional de-differentiation of said cell to be treated, said cell to be treated always remaining as a specialized functional cell that is immunologically autologous to the donor tissue from which said cell to be treated is derived, and for which the phenotype is preserved and/or rejuvenated.

In a first advantageous variation, the method comprises the following steps:

providing a cell to be treated;

providing a genetic reprogramming medium (GRM) comprising at least natural cytoplasm from at least one genetic reprogramming cell (GRC) and/or synthetic cytoplasm; and introducing said complete cell to be treated into said GRM to rejuvenate said cell to be treated by influences and/or interactions and/or exchanges between said cell to be treated and said GRM;

separating said rejuvenated cell from said GRM; and cultivating and multiplying said at least one rejuvenated cell.

Advantageously, before introducing the complete cell to be treated into said GRM, said complete cell to be treated undergoes a pretreatment in order to temporarily open one or more passage(s) in its membrane, allowing influences and/or interactions and/or exchanges between said pretreated cell and said GRM through said open passage(s) in the membrane of said pretreated cell.

Advantageously, said pretreatment of said cell to be treated causes pore opening or mechanical or physical cracking of said membrane.

Advantageously, during said pretreatment, said cell to be treated is immersed in a bath, especially saponin or streptolysin 0, then washed, in particular with a physiological solution.

Advantageously, said step of separating said rejuvenated cell from said GRM is carried out before the end of the first mitosis of said rejuvenated cell.

Advantageously, said GRM comprises an enucleated and activated oocyte.

Advantageously, the activating substances that are capable of activating nuclear metabolism, such as cells or cell extracts appearing during cicatrization and/or proteins or peptides for signaling or for stimulating the metabolism and/or growth factors and/or cells or extracts from cancer cells, are added during a pretreatment and/or added to said GRM and/or added during multiplication of the rejuvenated cells.

In accordance with another advantageous variation, the method comprises the following steps:

providing at least one stem cell or adult differentiated cell originating from a donor tissue; and introducing into said specialized adult cell, especially into its cytoplasm, siRNA specifically acting on HP1 heterochromatins, in particular anti HP1 siRNA, to inhibit RNA that controls the evolution of HP1 heterochromatins.

Advantageously, the step of introducing anti HP1 siRNA comprises simultaneously introducing anti HP1 α siRNA, anti HP1 β siRNA and anti HP1 γ siRNA.

Advantageously, said adult cell is a senescent cell, functional or non-functional, the introduction of anti HP1 siRNA causing the return of mitosis, in particular durable, viable and regenerative mitosis of said senescent cell.

Advantageously, after introducing the anti HP1 siRNA into the cell, the structural appearance of the HP1 heterochromatins becomes more homogenous and/or less anisotropic.

Advantageously, said cell to be treated is a viable senescent cell, functional or non-functional, rejuvenation causing the return of mitosis, in particular durable, viable and regenerative mitosis of said senescent cell.

Advantageously, the method is suitable for reprogramming adult cells such as thymus cells, heart cells, dendritic cells, adipose cells, auditory cells, ocular cells, olfactory cells, articular cells, renal cells, bone cells, dental cells, desmodontal cells, cartilage cells, bone cells, muscle cells, pancreatic cells, hepatic cells, nerve cells, prostate cells, hematopoietic cells, immune cells, lymphocytary cells, pulmonary cells, arterial cells, retinal cells, cutaneous cells, dermal cells, epidermal cells, conjunctival cells, glandular cells, tendon cells, vascular cells, spleen cells, parathyroid cells, suprarenal cells and/or cells of the digestive, respiratory and urinary tracts.

Advantageously, rejuvenation of said rejuvenated cell to be treated is measured by the analysis of markers associated with biological age, in particular the SAHF ("senescence associated heterochromatin foci") markers and/or the SASP ("senescence associated secretory phenotype") components, in particular the IL-6 component.

Advantageously, said method principally or solely modifies the biological age of said cell to be treated.

The advantages, characteristics and applications of the invention become apparent from the following detailed description of several implementations and variations of the invention.

In particular, the invention relates to partial epigenetic reprogramming, in particular retaining the monopotent state, of an adult biological cell, without it de-differentiating functionally and/or without it losing its original phenotype. In contrast, the aim of the invention is to be able to modify the biological age of the cells gradually, in particular to rejuvenate them, while keeping said cells at all times functional, specialized and immunologically autologous to the donor tissue from which the original cell derives, the phenotype of said cells being preserved and/or reinforced and/or rejuvenated.

In particular, the present invention relates to methods that are applicable to the field of functional and/or morphological cell treatments and/or repairs and/or improvements intended to open up many opportunities in the fight against diseases caused or promoted by advanced age, cell senescence, intoxication and tissue degeneracy resulting, for example, from chronic infections, atopies or wear and tear.

In particular, the present invention provides methods of treating cells of a tissue, in particular to rejuvenate and/or repair said cells. The cells may then be cultivated in a suitable medium, in vitro or in vivo, in order to create a stock or tissue of genetically and epigenetically partially reprogrammed differentiated cells that are capable of being implanted into the tissue under consideration or at a distance therefrom, where said cells can in particular release hormones, proteins and/or peptides for signaling and/or for stimulating the metabolism, and/or DNA repair enzymes for the tissue under consideration.

In known manner, DNA and its chromatins and heterochromatins can bind radicals (for example methyl or diacetyl radicals) that deactivate the normal functions of genes or histones with which they are associated. Cell reprogramming methods are known, such as the production of induced pluripotent cells (iPS), where the epigenetic type is changed into an embryonic epigenetic type. In contrast, the aim of the present invention is to principally or solely reverse those epigenetic modifications responsible for cell aging in a targeted manner, while retaining the functions of said cells. Thus, cells reprogrammed in accordance with the invention can retain their entire original phenotype. Said reprogramming is known as monopotent reprogramming.

It is also known to cause senescent cells, such as cells that no longer carry out mitosis, to divide once again. This has been described, for example, in the article "Critical requirement for cell cycle inhibitors in sustaining nonproliferative states" by D. Pajalunga et al; The Journal of Cell Biology; Vol 176; No 6; 12 Mar. 2007; pages 807 to 818. However, those methods cannot tell whether a short, non-physiological prolongation of the lifespan of the cell has been obtained or whether it has been durably, physiologically rejuvenated.

In accordance with one aspect of the invention, a complete cell to be treated, i.e. including in particular the nucleus, the cytoplasm, and the cell membrane, is temporarily introduced into an appropriate medium in which the cell is to be partially reprogrammed, in particular rejuvenated. This type of treatment is similar to that termed "partial cloning" by the inventor, previously described in documents WO 2005/046790 and US 2006/0252062.

More precisely, the invention is aimed at bringing a complete cell to be treated, preferably already pretreated, into contact with an appropriate genetic reprogramming medium (GRM) for a predetermined time. Thus, the complete cell is temporarily transferred into a GRM, rather than just its nucleus or a portion thereof, as described in the prior art documents mentioned above. The method is thus simplified considerably, since transfer of a complete cell into and out of a GRM, for example an enucleated and activated oocyte, is relatively easy using a micromanipulator, for example. In contrast, manipulation of a nucleus isolated from its cell is more complex and difficult. Moreover, this method means that mitochondrial and ribosomal RNA and DNA is easier to eliminate from the oocyte cytoplasm of the GRM in order to protect the immunological specificity of the nucleus of the cell to be treated that is in its own filtering cytoplasm. This method is also direct and rapid, typically of the order of a few days, as opposed to periods of several weeks for methods based on stem cells.

GRM comprises at least natural cytoplasm from at least one genetic reprogramming cell (GRC) and/or synthetic cytoplasm. Advantageously, the GRM comprises all or a portion of one or more GRCs. Such a GRC is then advantageously an oocyte, an embryonic cell, an embryonic or adult stem cell, a fetal cell, or a cell recipient reconstituted from said cells, or synthesized. In its simplest version, the GRM is formed by an enucleated and activated oocyte, in particular artificially enucleated and activated. A reconstituted and/or synthetic cytoplasm may in particular be composed of extracts from embryonic serums, from cicatrization and/or from cells undergoing metabolic activation and/or from cytoplasms from certain embryonic cancer cells. A totally synthetic cytoplasm is possible, for example produced by physical and chemical reconstitution of active substances. It is also possible to produce a GRM in the form of a GRC "liquor", with or without nuclei.

It is also possible to add to the GRM extracts from cells or from cytoplasm and/or other substances known for their capacity for activating nuclear metabolism, such as cells or extracts from cells appearing during cicatrization and/or proteins or peptides for signaling or stimulating the metabolism and/or growth factors and/or cancer cells or cell extracts. The cell or cytoplasm extracts may be obtained using well-known physical or chemical treatments. The advantage of using cancer cells, in particular cytoplasm therefrom, is explained by the fact that they have particularly intense metabolic, signaling and mitosis activation factors that are capable of temporarily inducing metabolic or nuclear activation of a cell to be treated. Contagion of the cancer is improbable since cancers are not generally transmissible to a different tissue and their cytoplasms generally remain normal. Other substances that may be added to the GRM include siRNA, which is described below, and/or proteins such as p53 and/or Chd1 proteins, and/or markers, such as the marker KI-67. Other substances comprise, for example, the genes KLF4 and C-myc supplemented with polyarginine radicals. Other protein factors are also possible.

Before introducing it into the GRM, the cell to be treated preferably undergoes a pretreatment, to temporarily open one or more passage(s) in the membrane of said cell. During contact with the GRM, exchanges occur between said GRM and said pretreated cell through said passages, causing partial reprogramming of said cell. Advantageously, the pretreatment is used to temporarily open the pores or cause mechanical or physical cracking of said cell membrane.

An advantageous pretreatment method consists in immersing said cell to be treated in a bath, especially of saponin or streptolysin 0, to cause pores to open temporarily, typically for several hours. This temporary opening is not toxic to the cell. Before transfer of the cell into the GRM, it is washed, for example using a physiological solution. Said washing does not interfere with the temporary opening of the pores.

In general, pretreatment of the cell to form passages or openings in the cell membrane may be of the chemical type (especially using saponin), physical type (especially using ultrasound or lasers, for example plasmon lasers), mechanical type (especially using piezoelectric needles or micro-needles, or using a flow of fluid with or without powder) or biological type (especially using bacterial, vegetable or mycosal secretions, for example toxins). A plasma laser, as described in the article by Rupert F. Oulton et al. ("Plasmon lasers at deep subwavelength scale", NATURE, advance online publication; 30 Aug. 2009; doi: 10.1038/nature08364; published online on 30 Aug. 2009), can be used to produce laser beams with an extremely reduced diameter, for example of the order of a nanometer. Microdissection lasers can also produce very small diameter beams.

The dimensions and shapes of said openings or passages in the cell membrane may, for example, be determined by appropriate dyes.

During temporary contact of the pretreated cell with the GRM, various molecules, proteins, peptides or the like may enter or leave the cell through the pores opened in the membrane. This means that partial reprogramming of the cell, in particular its epigenetic rejuvenation, can be carried out without loss of cell functions and the immune properties of said cell.

The pretreated cell is left in the GRM for a predetermined period then removed. Preferably, the pretreated cell is removed from the GRM before the end of nuclear telophase in the cell, i.e. before it divides into two cells, in other words before the end of its first mitosis. This is thus termed "partial cloning" or PCL. The contact period with the GRM may be optimized as a function of the desired degree of partial reprogramming. As an example, the GRM may be removed from the rejuvenated cell at anaphase for limited rejuvenation, or at telophase for more substantial rejuvenation.

Alternatively, cell rejuvenation as measured by the reduction of SAHF ("senescence associated heterochromatin foci") markers may be carried out with no cell mitosis.

The rejuvenated cell is then placed in a multiplication culture in order to obtain millions of rejuvenated differentiated cells, for example.

It should be noted that the activation substances mentioned above, which may be added to the GRM, could also be added as a replacement or supplement during one or more steps of the method, for example during pretreatment and/or to the multiplication culture.

In accordance with another implementation, siRNA ("small interfering RNA") are introduced into a cell, especially into its cytoplasm, which has the effect of blocking inhibition of certain target genes, reactivating them. More precisely, siRNA that acts specifically on HP1 heterochromatins, namely anti HP1 siRNA, may be introduced. This blocks or inhibits the RNA that controls the evolution of the HP1 types. When the cell is a quiescent senescent cell, the return of viable mitosis is observed. As explained above, said siRNA may also be introduced into the MRG for the implementation described above.

Preferably, anti HP1 $\alpha$ siRNA, anti HP1 $\beta$ siRNA and anti HP1 $\gamma$ siRNA are introduced simultaneously into the cell. Preferably, specific siRNA are also added to inhibit the p53, p21 and p19 genes. This causes not only a large number of mitoses, but they have a normalized appearance under optical microscopy.

It is now known that the constitution of heterochromatins and cell age are linked. This is deduced in particular from the article "Aging by epigenetics ● a consequence of chromatin damage?" by J. M. Sedivy et al.; Exp Cell Res.; 10 Jun. 2008; 314 (9): 1909-1917. Heterochromatin HP1, which exists in three forms, namely HP1 $\alpha$ heterochromatin, HP1 $\beta$ heterochromatin and HP1 $\gamma$ heterochromatin, is a condensed chromatin located close to the DNA. With age, larger blocks of heterochromatins are formed. The simultaneous introduction of anti HP1 siRNA not only causes the return of mitosis in a senescent cell, but it also modifies the structural appearance of the heterochromatins, rendering them less anisotropic and more homogenous. Such an effect may cause genuine rejuvenation of the cell. In fact, one of the causes of aging of a cell is the formation of foci of HP1 heterochromatins associated with senescence, known as SAHF ("senescence associated heterochromatin foci"). Here, these foci or clusters or bits of HP1 heterochromatins are at least partially eliminated, restoring a more homogenous appearance to said aged heterochromatins.

According to the author, anti HP1 $\alpha+\beta+\gamma$ type siRNA reduces the expression of HP1; in particular, they probably interfere with their transcription or translation.

It should also be noted that introducing siRNA into the cytoplasm of a cell provokes a temporary effect on said cell, which disappears after a few days, but its rejuvenating effect persists.

In accordance with another variation, selected messenger RNA (mRNA) may be introduced into a specialized adult cell to contribute thereby to the activation of specific genes, which increases cell rejuvenation. It is also possible to use micro-RNA, which does not in the end transform into proteins such as messenger RNA, but which due to their own constitution act to bring about certain epigenetic adjustments. These messenger RNA and/or these micro-RNA may be used in place of the siRNA, or along with it.

Preferably, this treatment is intended to rejuvenate the treated cell, but without de-differentiating it, and thus it retains all of its specificity. Hence, in known integral reprogramming methods, messenger RNA usually requires more than 20 days to bring the cell to the de-differentiated embryonic state.

In contrast, a genome analysis, for example using biochips, can rapidly detect activation of the desired genes and thus means that the targeted reprogramming of the genes responsible for senescence or functional failure of cells can be carried out. It may be advantageous to gradually reverse the cellular senescences in the reverse order of their appearance, which can be detected by successive examinations with specialized biochips. Thus, silenced genes can be reactivated gradually in the order of their extinction, either by activating them in groups by partial reprogramming or, if possible, gene by gene using targeted synthetic mRNA or micro-RNA or siRNA or RNA instead. It then becomes possible to combat genetic aging as it appears, and precisely at the level of the genes that are being silenced in succession.

Thus, one variation of the invention consists in reprogramming genetic expression and their epigenetic corollary, in order to act preferentially, commencing with the most recently inhibited genes, i.e. in a reverse chronological order from that of spontaneous aging. This means that progress and specific stability are tolerated as well as possible since the natural steps in the genetic evolution of the tissue are followed in reverse order along the same functional and/or local route. This requires firstly an analysis of spontaneous evolution in the genome to be treated and secondly an attempt to partially reverse the chronological order of biological time. This method is facilitated by the fact that the most recent genetic changes are usually the least stable and that probably, the function of the oocyte naturally respects this chronology of nuclear involution.

It would be possible to introduce one or more specific mini biochips, preferably rechargeable and capable of being read automatically, adapted to target genes in contact with the cell in vivo in order to periodically follow successive deactivation and activation brought about by the gene treatment. Implantation of such an automated device may be envisaged.

In order to introduce the messenger RNA and/or micro-RNA and/or siRNA into the cell, it is possible to use means for creating at least one opening in the pores in the membrane of said cell, and means, such as a pipette, for transferring messenger RNA and/or micro-RNA into said cell through said at least one opening or puncture. It is also possible to use an electroporation method and, in some circumstances, adenoviruses and certain other plasmids or cosmids that do not penetrate genomic DNA, or proteins from cell reprogramming gene factors termed piPS, which may act as cytoplasmic introducers for said selected factors. This may in particular be used as a complement to partial cloning.

All categories of RNA and polymerases are currently in principle capable of being synthesized and/or synthetically modified, which means that these factors can be produced in an even more effective genetic manner, for example with the aid of slight chemical modifications to certain radicals.

Another treatment may also be envisaged for causing modification of the biological age of a specialized adult cell, namely an ultrasound-based treatment. Using predetermined frequencies and amplitudes, it is possible to cause one or more of the radicals bound to the DNA or to its chromatins to resonate with the effect of regulating certain genes. This selective resonance means that certain radicals regulating the genes involved in cell rejuvenation can be changed in a targeted manner without affecting the other properties of the cell, in particular its specific phenotype. It should be noted that this method of treatment by ultrasound may be employed as a complement to the method of introducing messenger RNA and/or micro-RNA and/or siRNA into the cell, but it could also be used independently thereof.

In a variation, the cell to be treated may undergo treatments based on laser beams, for example a plasmon laser, or other beams such as microwaves, having the effect of changing certain radicals that regulate DNA and the histone code. Here again, these methods may be used as complements to those described above or independently thereof, to partially reprogram the cells to be treated in a more stable manner.

Advantageously, it is also possible to treat the cells with chemical substances, drugs, chemical agents such as co-repressors or specific RNA polymerases, which may be natural or synthetic, to activate certain genes, and/or agonists or antagonists for certain cellular metabolic reactions that can be used to inhibit or activate certain cellular metabolisms that are more generally associated with the biological age of the cells. As an example, it is possible to envisage the use of a chemical substance capable of demethylizing the cytosine of certain genes, dopamine to temporarily accelerate the metabolism, or beta-blockers to slow that metabolism down or to raise or lower the temperature. This category of treatment is advantageously complementary to those described above.

Advantageously, cell fusion may also be used to partially reprogram a cell epigenetically. Cell fusion consists in combining two whole cells (or parts of cells, such as the nucleus or cytoplasm). Thus, for example, by combining young cells with old cells or portions of cells (in particular specialized adult cells), the old cells may be partially rejuvenated.

The invention can thus potentialize the reprogramming without obtaining massive quantities of pluripotent cells, by using one or more of the following methods:
  1) introducing anti HP1 siRNA;
  2) introducing messenger RNA;
  3) introducing selected micro-RNA;
  4) partial cloning;
  5) simplified partial cloning;
  6) introducing certain drugs or chemical substances that are agonists or antagonists for certain genetic or epigenetic biochemical cell reactions;
  7) radiation: selective ultrasound, microwaves or lasers;
  8) cell fusion;
  9) exchange of chromosomes between an adult cell and a rejuvenated cell.

These various means, separately or in various combinations, may also act to change certain unwanted factors that may disturb partial reprogramming.

In a variation of the invention, gradual partial cell reprogramming is carried out such that said reprogramming does not stray too far from the desired biological age. To this end, the introduction of active factors into the cells to be treated is carried out either in a plurality of successive doses of all of these factors or by initially applying a fraction of said factors and subsequently another fraction of the active factors. The temporary introduction or contact of cells can always be combined, either in an oocyte or its extracellular extract, or in certain embryonic or cancerous cells or extracts thereof. Said partial and progressive cell reprogramming steps mean that reprogramming can be gradual, and almost in real time, for example employing markers or frequent inspections.

The present invention may be applied without limitation to the partial, stable epigenetic regeneration of any specialized adult cell such as thymus cells, heart cells, dendritic cells, adipose cells, auditory cells, ocular cells, olfactory cells, articular cells, renal cells, bone cells, dental cells, desmodontal cells, cartilage cells, bone cells, muscle cells, pancreatic cells, hepatic cells, nerve cells, prostate cells, hematopoietic cells, immune cells, pulmonary cells, arterial cells, retinal cells, cutaneous cells, dermal cells, epidermal cells, conjunctival cells, glandular cells, tendon cells, vascular cells, spleen cells, parathyroid cells, suprarenal cells and/or cells of the digestive, respiratory and urinary tracts.

It may be desirable to partially reprogram, together or separately with subsequent assembly, a plurality of cells representing an organic functional unit such as a nephron, pigmentary retinal cells of various categories or pulmonary alveolas, for example, to form a rejuvenated organic functional unit.

Many applications of the system and the method of the invention may be envisaged, in particular (the list is not limiting) to treat renal insufficiency, degenerative diseases of the joints such as arthritis, or osteoporosis, subjects who have suffered severe inflammation, especially by reactional weakening of various lymphocytes producing antibodies and pro- and anti-inflammatory cytokines, to improve anticancer treatments, to treat ulcers, to combat senescence of the skin on a genetic level by modifying collagens and enhancing the rate and quality of cicatrization and dermal, epidermal and subcutaneous connective tissue repairs, especially to rejuvenate them, to improve the thickness and elasticity of the skin, to regenerate necrotized, fibrotic or inactive zones of tissue, for example in the myocardium, especially as a result of an infarctus or severe cardiac insufficiency or, for example, an organ that has developed a tumor targeted by a destructive anti-cancer treatment, to aid in the determination of the mechanism responsible for problems with the health of a mammal, especially to reduce its biological age to evaluate or determine the time at which a disease grips, to treat diseases characterized by a cellular deficit, to promote maintenance of an implant in a joint or a bone by means of an envelope or simple framework or to support regenerated cells, to ensure good histocompatibility and morphocompatibility between a graft and a donor and in particular bone, joint and vertebral prostheses, in particular to improve fixing of metallic, ceramic, plastic and/or biological implants, to limit rejection of non-autologous grafts by the recipient, to rejuvenate retinal and ocular tissues, etc.

One particular application relates to the tissues of the thymus, existing or to be recreated genetically by cell reprogramming and/or forced transcription, and B and T lymphocytes. The methods of the present invention can be used to rejuvenate the defenses of organs and tissues from the donor against autoimmune diseases and infections that increase with age. It is also possible to carry out a selective treatment of the B and T lymphocytes during which they undergo the partial epigenetic reprogramming of the invention, by adding antigens (for example antibiotic-resistant staphylococci) to incite the lymphocyte to develop specific antibodies against said antigens. If the cell survives, it must have developed effective antibodies. As an example, antigens immobilized on a matrix may be selected in order to bring them into contact with specific T lymphocytes that have been rejuvenated in accordance with the invention. It is also possible to envisage a treatment of immunoactive cells such as B and T lymphocytes, dendritic cells and ganglion or spleen lymphoids in order to prevent a lesion or tissue destruction caused by autoimmune or degenerative diseases.

Another particular application relates to the cells of the myocardium which, once rejuvenated using one or more of the methods of the invention, may be used for electrostimulation as described in document WO 2005/046790.

Yet another particular application relates to fibroblasts, which may be multiplied after rejuvenation, retaining all of the cell properties and functions. Said multiplication may then form a rejuvenated tissue that can be re-implanted into the original tissue. Optionally, the rejuvenated cells may be associated with a few aged cells to improve implantation.

It should be noted that the modification of the biological age of a cell (rejuvenation or aging) may be evaluated by various methods and markers. Hence, it is possible to employ the analysis of markers associated with biological age, in particular SAHF ("senescence associated heterochromatin foci") markers and/or the SASP ("senescence associated secretory phenotype") components, especially the IL-6 component. This also applies with the analysis of cell cycle inhibitors, such as p53 or p21 proteins. Further, for some cells, the times or rates at which a cell can recover its membrane potential and its action potential after a challenge (such as a loss of oxygen or a slight excess of potassium) may be compared before and after treatment. If the recovery time is shorter, then the cell is functionally rejuvenated. Other methods consist in comparing, before and after treatment, mitosis repetition rates, mitosis rates or the appearance of mitosis per se, cicatrization rates, or modifications to the dimensions (volume and/or length) of the telomers, the use of staining or non-staining biochemical markers, a study of cell functions, resistance to toxins and infections, etc. It should be noted that no currently known method can provide a precise and absolute measure of biological age, but rather an indication thereof.

While the present invention has been described with reference to various aspects thereof, and by means of a variety of examples of its application, this is not intended to be a limitation thereto; the skilled person is capable of providing a variety of modifications.

The invention claimed is:

1. A method of genetic and epigenetic reprogramming of biological cells, which reprograms at least one cell without returning it to its embryonic state, said method comprising:
    (a) providing at least one cell, wherein said cell is a stem cell or an adult differentiated cell isolated from a donor tissue;
    (b) introducing into the cytoplasm of said cell an siRNA specific for a Heterochromatin protein 1α (HP1α), an siRNA specific for a Heterochromatin protein 1β (HP1β), and an siRNA specific for a Heterochromatin protein 1γ (HP1γ), to thereby decrease expression of said HP1α, HP1β and HP1γ, wherein the introduction of said siRNAs specific for HP1α, HP1β and HP1γ rejuvenates said cell by modifying the biological age of said cell without causing functional de-differentiation of said cell, with said cell remaining as a specialized functional cell that is immunologically autologous to said donor tissue,
    and wherein the rejuvenated cell exhibits a decrease in Senescence-Associated Heterochromatin Foci (SAHF)

markers and/or Senescence-Associated Secretory Phenotype (SASP) components, as compared to the cell before rejuvenation.

2. A method of genetic and epigenetic reprogramming of biological cells, which reprograms at least one cell without returning it to its embryonic state, said method comprising:
   (a) providing at least one cell, wherein said cell is an adult differentiated cell isolated from a donor tissue, and wherein said adult cell is a functional or non-functional senescent cell;
   (b) introducing into the cytoplasm of said cell an siRNA specific for a Heterochromatin protein 1 (HP1), to thereby decrease expression of said HP-1, wherein the introduction of said siRNA into said cell triggers the return of mitosis in said cell, and wherein the introduction of said siRNA rejuvenates said cell by modifying the biological age of said cell without causing functional de-differentiation, with said cell remaining as a specialized functional cell that is immunologically autologous to said donor tissue,
   and wherein the rejuvenated cell exhibits a decrease in Senescence-Associated Heterochromatin Foci (SAHF) markers and/or Senescence-Associated Secretory Phenotype (SASP) components, as compared to the cell before rejuvenation.

3. A method of genetic and epigenetic reprogramming of biological cells, which reprograms at least one cell without returning it to its embryonic state, said method comprising:
   (a) providing at least one cell, wherein said cell is a stem cell or an adult differentiated cell isolated from a donor tissue;
   (b) introducing into the cytoplasm of said cell an siRNA specific for a Heterochromatin protein 1 (HP1), to thereby decrease expression of said HP-1, wherein the introduction of said siRNA into said cell causes the structural appearance of HP1 heterochromatins in said cell to become more homogenous and/or less anisotropic, and wherein the introduction of said siRNA rejuvenates said cell by modifying the biological age of said cell without causing functional de-differentiation, with said cell remaining as a specialized functional cell that is immunologically autologous to said donor tissue,
   and wherein the rejuvenated cell exhibits a decrease in Senescence-Associated Heterochromatin Foci (SAHF) markers and/or Senescence-Associated Secretory Phenotype (SASP) components, as compared to the cell before rejuvenation.

4. A method of genetic and epigenetic reprogramming of biological cells, which reprograms at least one cell without returning it to its embryonic state, said method comprising:
   (a) providing at least one cell isolated from a donor tissue, wherein said cell is viable and is a functional or non-functional senescent cell;
   (b) introducing into the cytoplasm of said cell an siRNA specific for a Heterochromatin protein 1 (HP1), to thereby decrease expression of said HP-1, wherein the introduction of said siRNA into said cell triggers the return of mitosis in said cell, and wherein the introduction of said siRNA rejuvenates said cell by modifying the biological age of said cell without causing functional de-differentiation, with said cell remaining as a specialized functional cell that is immunologically autologous to said donor tissue,
   and wherein the rejuvenated cell exhibits a decrease in Senescence-Associated Heterochromatin Foci (SAHF) markers and/or Senescence-Associated Secretory Phenotype (SASP) components, as compared to the cell before rejuvenation.

5. A method of genetic and epigenetic reprogramming of biological cells, which reprograms at least one cell without returning it to its embryonic state, said method comprising:
   (a) providing at least one cell, wherein said cell is a stem cell or an adult differentiated cell isolated from a donor tissue;
   (b) introducing into the cytoplasm of said cell an siRNA specific for a Heterochromatin protein 1 (HP1), to thereby decrease expression of said HP-1, wherein the introduction of said siRNA rejuvenates said cell by modifying the biological age of said cell without causing functional de-differentiation, with said cell remaining as a specialized functional cell that is immunologically autologous to said donor tissue; and
   (c) measuring the rejuvenation of said cell by analyzing one or more Senescence-Associated Heterochromatin Foci (SAHF) markers and/or one or more Senescence-Associated Secretory Phenotype (SASP) components, wherein the rejuvenated cell exhibits a decrease in Senescence-Associated Heterochromatin Foci (SAHF) markers and/or Senescence-Associated Secretory Phenotype (SASP) components, as compared to the cell before rejuvenation.

6. The method according to claim 1, wherein said cell is selected from the group consisting of: thymus cells, heart cells, dendritic cells, adipose cells, auditory cells, ocular cells, olfactory cells, articular cells, renal cells, bone cells, dental cells, desmodontal cells, cartilage cells, bone cells, muscle cells, pancreatic cells, hepatic cells, nerve cells, prostate cells, hematopoietic cells, immune cells, lymphocytary cells, pulmonary cells, arterial cells, retinal cells, cutaneous cells, dermal cells, epidermal cells, conjunctival cells, glandular cells, tendon cells, vascular cells, spleen cells, parathyroid cells, suprarenal cells and/or cells of the digestive, respiratory and urinary tracts.

7. The method according to claim 2, wherein said cell is selected from the group consisting of: thymus cells, heart cells, dendritic cells, adipose cells, auditory cells, ocular cells, olfactory cells, articular cells, renal cells, bone cells, dental cells, desmodontal cells, cartilage cells, bone cells, muscle cells, pancreatic cells, hepatic cells, nerve cells, prostate cells, hematopoietic cells, immune cells, lymphocytary cells, pulmonary cells, arterial cells, retinal cells, cutaneous cells, dermal cells, epidermal cells, conjunctival cells, glandular cells, tendon cells, vascular cells, spleen cells, parathyroid cells, suprarenal cells and/or cells of the digestive, respiratory and urinary tracts.

8. The method according to claim 3, wherein said cell is selected from the group consisting of: thymus cells, heart cells, dendritic cells, adipose cells, auditory cells, ocular cells, olfactory cells, articular cells, renal cells, bone cells, dental cells, desmodontal cells, cartilage cells, bone cells, muscle cells, pancreatic cells, hepatic cells, nerve cells, prostate cells, hematopoietic cells, immune cells, lymphocytary cells, pulmonary cells, arterial cells, retinal cells, cutaneous cells, dermal cells, epidermal cells, conjunctival cells, glandular cells, tendon cells, vascular cells, spleen cells, parathyroid cells, suprarenal cells and/or cells of the digestive, respiratory and urinary tracts.

9. The method according to claim 4, wherein said cell is selected from the group consisting of: thymus cells, heart cells, dendritic cells, adipose cells, auditory cells, ocular cells, olfactory cells, articular cells, renal cells, bone cells, dental cells, desmodontal cells, cartilage cells, bone cells, muscle cells, pancreatic cells, hepatic cells, nerve cells, prostate cells, hematopoietic cells, immune cells, lymphocytary cells, pulmonary cells, arterial cells, retinal cells, cutaneous cells, dermal cells, epidermal cells, conjunctival cells, glandular cells, tendon cells, vascular cells, spleen cells, parathyroid cells, suprarenal cells and/or cells of the digestive, respiratory and urinary tracts.

10. The method according to claim 5, wherein said cell is selected from the group consisting of: thymus cells, heart cells, dendritic cells, adipose cells, auditory cells, ocular cells, olfactory cells, articular cells, renal cells, bone cells, dental cells, desmodontal cells, cartilage cells, bone cells, muscle cells, pancreatic cells, hepatic cells, nerve cells, prostate cells, hematopoietic cells, immune cells, lymphocytary cells, pulmonary cells, arterial cells, retinal cells, cutaneous cells, dermal cells, epidermal cells, conjunctival cells, glandular cells, tendon cells, vascular cells, spleen cells, parathyroid cells, suprarenal cells and/or cells of the digestive, respiratory and urinary tracts.

* * * * *